United States Patent
Kononen et al.

(10) Patent No.: US 6,699,710 B1
(45) Date of Patent: Mar. 2, 2004

(54) TUMOR TISSUE MICROARRAYS FOR RAPID MOLECULAR PROFILING

(75) Inventors: Juha Kononen, Rockville, MD (US); Stephen B. Leighton, Silver Spring, MD (US); Olli-P. Kallioniemi, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/622,686

(22) PCT Filed: Feb. 24, 1999

(86) PCT No.: PCT/US99/04001

§ 371 (c)(1), (2), (4) Date: Oct. 12, 2000

(87) PCT Pub. No.: WO99/44063

PCT Pub. Date: Sep. 2, 1999

Related U.S. Application Data

(60) Provisional application No. 60/075,979, filed on Feb. 25, 1998.

(51) Int. Cl.⁷ .......................... C12M 1/00; C12M 1/36; G01N 15/06
(52) U.S. Cl. .................. 435/283.1; 435/286.2; 435/288.7; 435/294.1; 422/50; 422/61; 422/68.1; 422/82.05; 700/95
(58) Field of Search .................. 435/294.1, 283.1, 435/286.2, 174, 288.7; 422/50, 61, 68.1, 82.05; 700/95

(56) References Cited

U.S. PATENT DOCUMENTS

| | | | |
|---|---|---|---|
| 4,684,613 A | * 8/1987 | Barrere et al. | 435/301 |
| 4,820,504 A | 4/1989 | Battifora | 424/3 |
| 4,914,022 A | 4/1990 | Furmanski et al. | 435/7 |
| 5,002,377 A | 3/1991 | Battifora et al. | 350/535 |
| 5,355,439 A | 10/1994 | Bernstein et al. | |

(List continued on next page.)

FOREIGN PATENT DOCUMENTS

| | | |
|---|---|---|
| GB | 2 197 471 | 5/1998 |
| WO | WO 98/44333 | 10/1998 |
| WO | WO 99/44062 | 9/1999 |

OTHER PUBLICATIONS

Webster's New Collegiate Dictionary, Merriam Webster, Inc. 1991, p. 96.*

Kraaz et al., "Multiblock: an aid in diagnostic immunohistochemistry," *J. Clin. Pathol.* 41:1377 (1988).

(List continued on next page.)

*Primary Examiner*—B J Forman
(74) *Attorney, Agent, or Firm*—Klarquist Sparkman, LLP

(57) ABSTRACT

An array-based technology facilitates rapid correlated gene copy number and expression profiling of very large numbers of human tumors. Hundreds of cylindrical tissue biopsies (diameter 0.6 mm) from morphologically representative regions of individual tumors can be arrayed in a single paraffin block. Consecutive sections from such arrays provide targets for parallel in situ visualization and quantitation of DNA, RNA or protein targets. For example, amplifications of six loci (mybL2, erbB2, Cyclin-D1, myc, 17q23 and 20q13) were rapidly determined by fluorescence in situ hybridization from 372 ethanol-fixed breast cancers. Stratification of tumors by estrogen receptor and p53 expression data revealed distinct patterns of gene amplification in the various subgroups of breast cancer that may have prognostic utility. The tissue array technology is useful in the rapid molecular profiling of hundreds of normal and pathological tissue specimens or cultured cells.

20 Claims, 10 Drawing Sheets

U.S. PATENT DOCUMENTS

| | | | |
|---|---|---|---|
| 5,614,415 A | | 3/1997 | Markin |
| 5,675,715 A | * | 10/1997 | Bernstein et al. ............. 395/82 |
| 5,700,637 A | | 12/1997 | Southern ...................... 435/6 |
| 5,746,855 A | | 5/1998 | Bolles |
| 6,103,192 A | | 8/2000 | Stapleton et al. |
| 6,103,518 A | * | 8/2000 | Leighton |
| 6,136,592 A | | 10/2000 | Leighton ................ 435/288.7 |
| 6,383,801 B1 | * | 5/2002 | Leighton |

OTHER PUBLICATIONS

Battifora et al., *Lab. Invest.* 55:244–248 (1986).
Wan et al., *J. Immunol. Meth.* 103:121–129 (1987).
Battifora and Mehta, *Lab. Invest.* 63:722–724 (1990).
Green and Olson, *PNAS USA* 87:1213–1217 (1990).
Miller and Groothuis, *Am. J. Clin. Pathol.* 96:228–232 (1991).
Pretlow et al., *J. Natl. Cancer Inst.* 3:394–398 (1993).
Sundblad, *Am. J. Clin. Pathol.* 102:192–193 (1993).
Tanner et al., *Cancer Res.* 54:4257–4260 (1994).
Schena et al., *Science*, 270:467–470 (1995).
Velculescu et al., *Science* 270:484–487 (1995).
Schena, *BioEssays*, 18(5):427–431 (1996).
Barlund et al., *Genes Chrom. Cancer* 20:372–376 (1997).
Moch et al., *Hum. Pathol.* 28:1255–1259 (1997).
Soares, *Cur. Opp. In Biotechnol.* 8:542–546 (1997).
Ramsay, *Nature Biotechnol.* 16:14–44 (1998).
Service, *Science*, 282:396–399 (1998).
Enghardt et al., *The Journal of Histotechnology* Vol 18(1):51–55, 1995.
Lampkin et al., *The Journal of Histotechnology* 13(2):121–123, 1990.
Press et al., *Cancer Research* 54:2771–2777, 1994.
Press et al., *Journal of Clinical Oncology* 15(8):2894–2903, 1997.

* cited by examiner

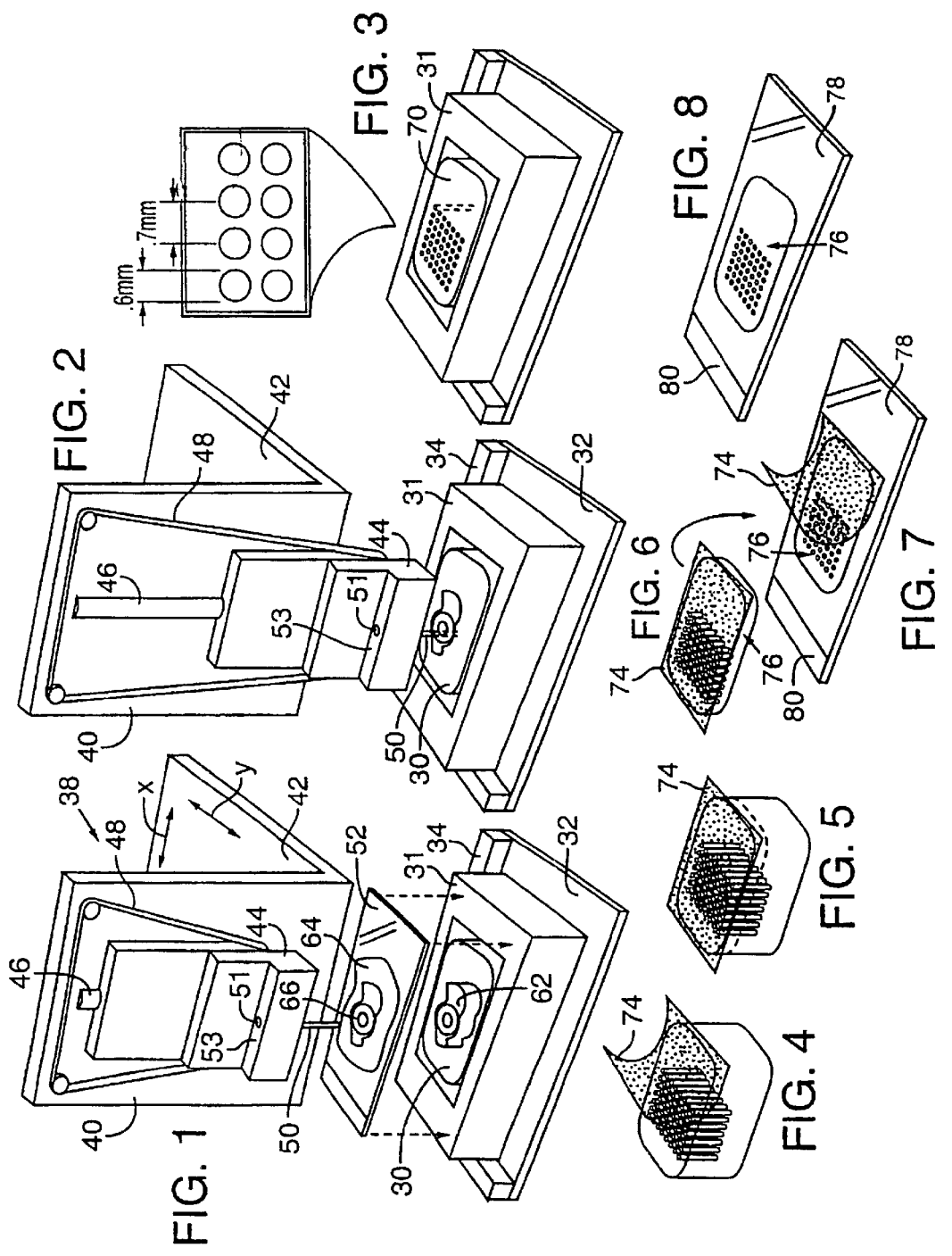

FIG. 10A
FIG. 10B
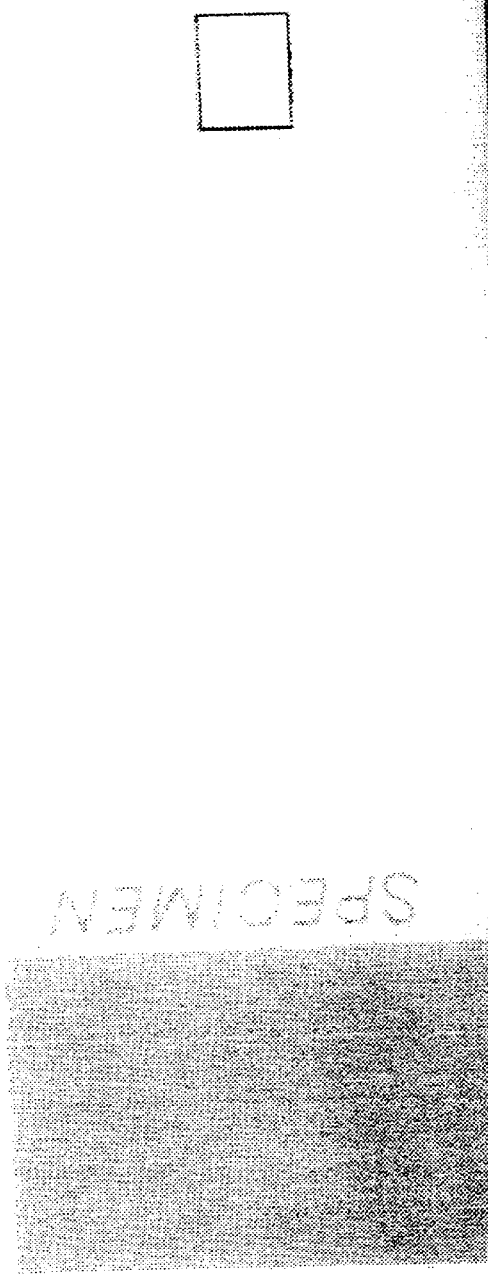
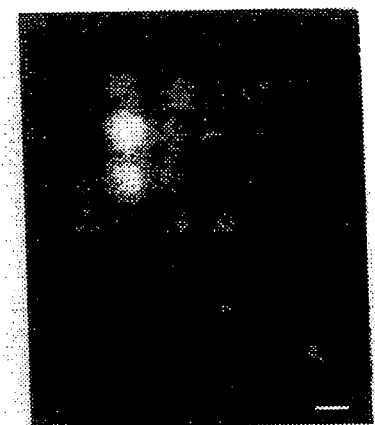
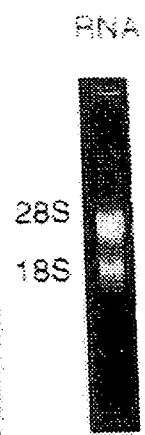
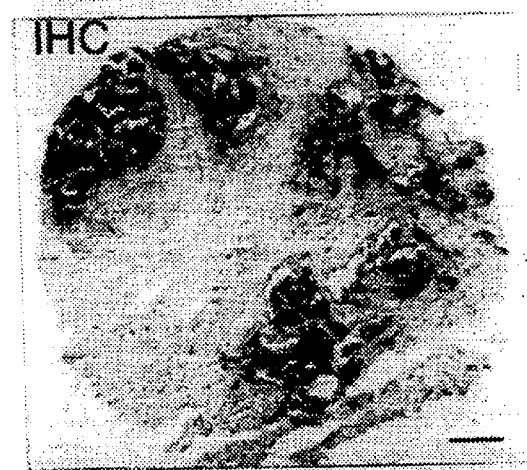
FIG. 10C
FIG. 10D
FIG. 10E

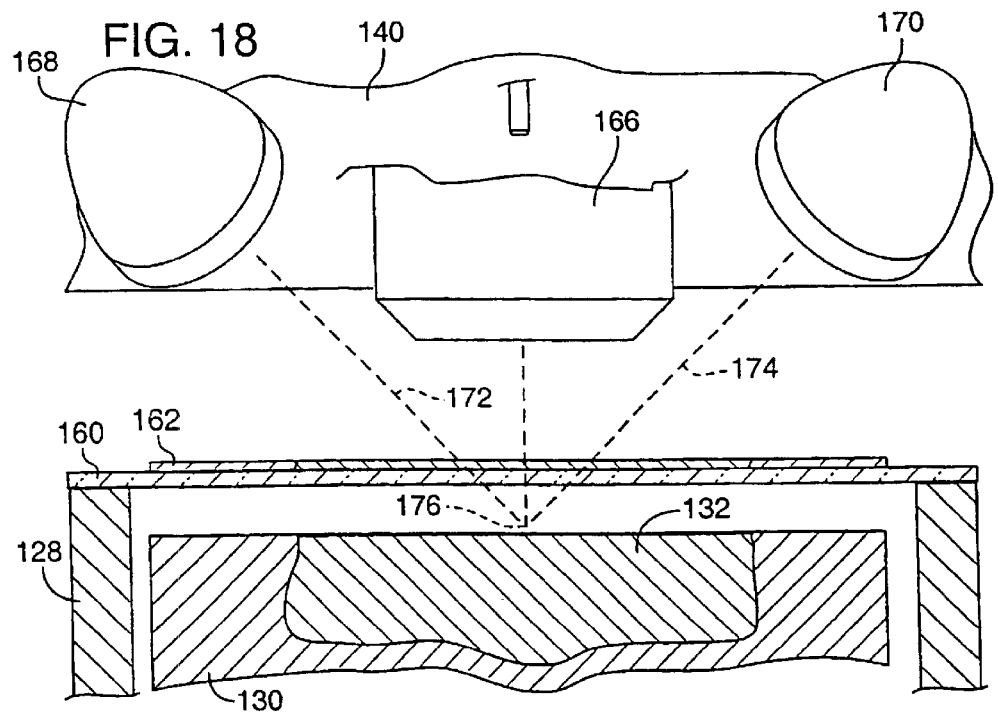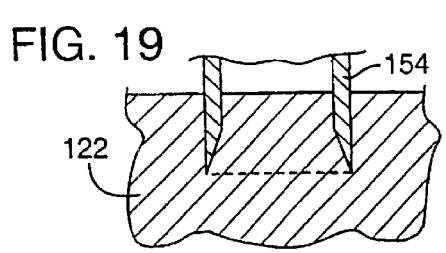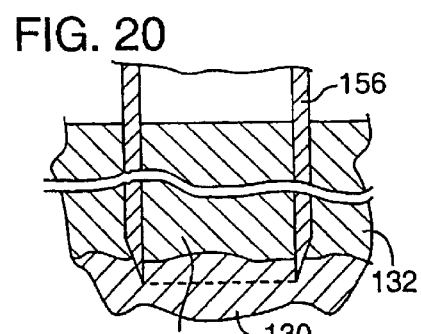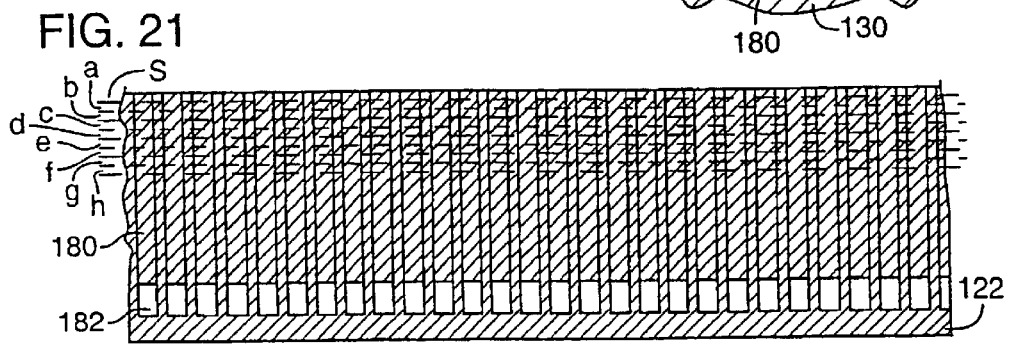

TUMOR TISSUE MICROARRAYS FOR RAPID MOLECULAR PROFILING

PRIORITY CLAIM

This application was filed as a 35 U.S.C. §371 application of PCT International Application No. US99/04001 filed Feb. 24, 1999, which designated the United States and was published in English under PCT Article 21(2), and which in turn claims benefit of U.S. Provisional Application 60/075,979, filed Feb. 25, 1998.

FIELD OF THE INVENTION

The present invention concerns devices for the microscopic, histologic and/or molecular analysis of tissue specimens.

BACKGROUND OF THE INVENTION

Biological mechanisms of many diseases have been clarified by microscopic examination of tissue specimens. Histopathological examination has also permitted the development of effective medical treatments for a variety of illnesses. In standard anatomical pathology, a diagnosis is made on the basis of cell morphology and staining characteristics. Tumor specimens, for example, can be examined to characterize the tumor type and predict whether the patient will respond to a particular form of chemotherapy. Although this microscopic examination and classification of tumors has improved medical treatment, the microscopic appearance of a tissue specimen stained by standard methods (such as hematoxylin and eosin) can often only reveal a limited amount of diagnostic or molecular information.

Recent advances in molecular medicine have provided an even greater opportunity to understand the cellular mechanisms of disease, and select appropriate treatments with the greatest likelihood of success. Some hormone dependent breast tumor cells, for example, have an increased expression of estrogen receptors on their cell surfaces, which indicates that the patient from whom the tumor was taken will likely respond to certain anti-estrogenic drug treatments. Other diagnostic and prognostic cellular changes include the presence of tumor specific cell surface antigens (as in melanoma), the production of embryonic proteins (such as α-fetoprotein in liver cancer and carcinoembryonic glycoprotein antigen produced by gastrointestinal tumors), and genetic abnormalities (such as activated oncogenes in tumors). A variety of techniques have evolved to detect the presence of these cellular abnormalities, including immunophenotyping with monoclonal antibodies, in situ hybridization with probes, and DNA amplification using the polymerase chain reaction (PCR).

The development of new molecular markers, however, has been impeded by the inability to group a large number of tissues within a small surface area Only a limited amount of hybridoma supernatant may be available, particularly during the early phase of monoclonal antibody generation, which limits the number of specimens that can be analyzed. Even if large quantities of the immunohistologic agent are available, however, the reagents are expensive and may vary in reactivity. These problems led Battifora et al. to propose in *Lab. Invest.* 5:244–248 (1986), and in U.S. Pat. No. 4,820,504, that multiple tissue specimens may be grouped together on a single slide to enable the specimens to be simultaneously screened by application of a single drop of hybridoma supernatant. The specimens were prepared by using a hand-held razor blade to cut deparaffinized and dehydrated tissue specimens into slices, which were then bundled together randomly, wrapped in a sausage casing, and re-embedded in paraffin. This technique required a high degree of manual dexterity, and incorporated samples into a composite block in a manner that made it difficult to find and identify particular specimens of interest.

A modification of this process was disclosed by Wan et al., *J. Immunol. Meth.* 103:121–129 (1987). and Furmanski et al. in U.S. Pat. No. 4,914,022, in which cores of paraffin embedded tissue were obtained from standard tissue blocks. The cores were softened and straightened by manually rolling them on a warm surface and then bundled inside a conventional drinking straw. This method was said to be suitable for simultaneous histologic testing of multiple tissue specimens, for example in the characterization of monoclonal antibodies. The technique of Miller and Groothuis, *A.J.C.P.* 96:228–232 (1991) similarly rolled tissue strips into "logs" from which transverse sections were taken to be embedded in paraffin. The straw and log techniques, however, were labor intensive, required a high degree of manual dexterity, and also randomly arranged the samples in a manner that complicated the identification of specimens of interest Battifora and Mehta, *Lab. Invest.* 63:722–724 (1990), and U.S. Pat. No. 5,002,377, attempted to overcome some of the problems of random placement by cutting specimens into a plurality of narrow strips, which were individually positioned in parallel rectangular grooves in a mold. The tissue strips were embedded in agar gel that was poured into the grooves to produce a plate-like member with a series of ridges. Several of the ridged plates were stacked together and embedded in paraffin to form a tissue block. A similar approach was proposed by Sundblad, *A.J.C.P.* 102:192–193 (1993), in which the tissue strips were placed in triangular wedges instead of rectangular grooves. Slicing the tissue, assembling it into rows, and embedding it in several steps to form the block was a time-consuming method that reduced the efficiency of examining a large number of tissue specimens.

All of these techniques have been inadequate for the efficient preparation of an array of tissue specimens that can be used for rapid parallel analysis of a variety of independent molecular markers. This inefficiency has been a significant problem in fields such as cancer research, because cancer development and progression is a multi-step process that involves sequential losses, rearrangements and amplifications of several chromosomal regions and multiple genes. These events lead to a dysregulation of critical signal transduction pathways for cell growth, death, and differentiation. The details of this complex process remain incompletely understood, partly because high-throughput strategies and techniques for analyzing such genetic changes in large numbers of uncultured human tumors have not been available.

For example, simultaneous analysis of several genes within the same or related signal transduction pathways may be necessary to pinpoint critical, rate-limiting steps in the dysregulation of cancer cell growth. Furthermore, analysis of structural and numerical changes affecting several chromosomes, loci and genes at the same time may be needed to understand the patterns of accumulation of genetic changes in different stages of the cancer progression. Finally after novel genes and genetic changes of potential importance in cancer have been identified, substantial additional research is usually required to determine the diagnostic, prognostic and therapeutic significance of these molecular markers in clinical oncology.

Since the amount of tissue often becomes rate limiting for such studies, the ability to efficiently procure, fix, store and distribute tissue for molecular analysis in a manner that minimizes consumption of often unique, precious tumor specimens is important. It is therefore an object of this invention to perform large-scale molecular profiling of tissue specimens (such as tumors) with minimal tissue requirements, in a manner that allows rapid parallel analysis of molecular characteristics (such as gene dosage and expression) from hundreds of morphologically controlled tumor specimens.

SUMMARY OF THE INVENTION

The foregoing objects are achieved by a method of parallel analysis of tissue specimens, in which a plurality of donor specimens are placed in assigned locations in a recipient array, and a plurality of sections are obtained from the recipient array so that each section contains a plurality of donor specimens that maintain their assigned locations. A different histological analysis is performed on each section, to determine if there are correlations between the results of the different analyses at corresponding locations of the array. In particular embodiments, the donor specimen is obtained by boring an elongated sample, such as a cylindrical core, from donor tissue, and placing the donor specimen in a receptacle of complementary shape, such as a cylindrical core, in the recipient array. Analyses that may be performed on the donor specimens include immunological analysis, nucleic acid hybridization, and clinicopathological characterization of the specimen.

In a more particular embodiment of the method, a recipient block is formed from a rigid embedding medium such as paraffin that can be cut with a punch or microtome, and a separate donor block is also formed by embedding a biological specimen in the embedding medium. Cylindrical receptacle cores are bored in the recipient block to form an array of receptacles at fixed positions, and cylindrical donor sample cores are obtained from the embedded biological specimen in the donor blocks The donor sample cores are then placed in the cylindrical receptacles at assigned locations in the array, and the recipient block is sliced to obtain a cross-section of the donor sample cores in the array, without disrupting the assigned array locations. A different histological analysis may be performed on each section, for example by using different monoclonal antibodies that recognize distinct antigens, or a combination of antigenically distinct monoclonal antibodies and nucleic acid (e.g. RNA and DNA) probes on sequential sections. The result of each distinct histological analysis in each position of the array is compared, for example to determine if a tissue that expresses an estrogen receptor also has evidence that a particular oncogene has been activated.

In a more particular embodiment of the method, a recipient block is formed from a rigid embedding medium such as paraffin that can be cut with a punch or microtome, and a separate donor block is also formed by embedding a biological specimen in the embedding medium. Cylindrical receptacle cores are bored in the recipient block to form an array of receptacles at fixed positions, and cylindrical donor sample cores are obtained from the embedded biological specimen in the donor block. The donor sample cores are then placed in the cylindrical receptacles at assigned locations in the array, and the recipient block is sliced to obtain a cross-section of the donor sample cores in the array, without disrupting the assigned array locations. A different histological analysis may be performed on each section, for example by using different monoclonal antibodies that recognize distinct antigens, or a combination of antigenically distinct monoclonal antibodies and nucleic acid (e.g. RNA and DNA) probes on sequential sections. The result of each distinct histological analysis in each position of the array is compared, for example to determine if a tissue that expresses an estrogen receptor also has evidence that a particular oncogene has been activated. The presence or absence of the estrogen receptor and oncogene can then be correlated with clinical or pathological information about the tissue (such as the presence of metastatic disease or the histological grade of a tumor). This simultaneous parallel analysis of multiple specimens helps clarify the inter-relationship of multiple molecular and clinical characteristics of the tissue.

The invention also includes a method of obtaining small elongated samples of tissue from a tissue specimen, such as a tumor, and subjecting the specimen to laboratory analysis, such as histological or molecular analysis. The elongated tissue sample can be taken from a region of interest of the tissue specimen, and the size of the sample is small enough that the characterstic being analyzed is substantially homogenous throughout the small sample. In a disclosed embodiment, the sample is a cylindrical sample punched from the tissue specimen, wherein the cylindrical specimen is about 14 mm long, and has a diameter of about 0.14 mm, for example about 0.3–2.0 mm. In specific embodiments, the cylinder diameter is less than about 1.0 mm, for example 0.6 mm. The sample is preferably preserved in a manner (such as ethanol fixation) that does not interfere with analysis of nucleic acids, and the sample can therefore be subjected to any type of molecular analysis, such as any type of molecular analysis based on isolated DNA or RNA.

The invention also includes an apparatus for preparing specimens for parallel analysis of sections of biological material arrays. The apparatus includes a platform, a tissue donor block on the platform, and a punch that punches or bores a tissue specimen from the donor block. The platform can also carry a recipient block in which the punch forms an array of receptacles at selected positions. Each receptacle can be positioned so that a tissue specimen can be expelled from the reciprocal punch into the receptacle. An x-y positioning device incrementally moves the punch or recipient block with respect to one another as the punch reciprocates, to form the receptacle array. The x-y positioning device also aligns sequential receptacles of the recipient block with the punch to deliver tissue specimens from the punch into the receptacle. A stylet may be introduced into the punch to expel the contents of the punch, which may be either paraffin from the recipient block or tissue from the donor block. Regions of interest of the tissue specimen are located by positioning a thin section slide over the donor block, to align structures of interest in the thin section slide with corresponding tissue specimen regions in the donor block.

The invention also includes a computer implemented system for parallel analysis of consecutive sections of tissue arrays, in which an x-y positioning platform moves a tray to a plurality of coordinates that correspond to positions in a recipient block array. A receptacle punch then punches a receptacle core from a recipient block on the positioning platform, and a stylet expels the receptacle core from the receptacle punch. A donor punch (which may be the same or separate from the recipient punch) punches a donor specimen from a donor block on the positioning platform, and a stylet expels the donor specimen from the donor punch into the receptacle as the donor punch is introduced into the receptacle. The donor specimen suitably has a diameter that is substantially the same as the diameter of the receptacle, so that the donor specimen fits securely in the receptacle. The computer system identifies the tissue by its location in the recipient array, so that when the donor block is sectioned a corresponding position in each sectional array will contain tissue from the identical donor specimen.

The foregoing and other objects, features, and advantages of the invention will become more apparent from the following detailed description of preferred embodiments which proceeds with reference to the accompanying drawings.

BRIEF DESCRIPTION OF THE DRAWINGS

FIG. 1 is a schematic perspective view of a first embodiment of the punch device of the present invention, showing alignment of the punch above a region of interest of donor tissue in a donor block.

FIG. 2 is a view similar to FIG. 1, but in which the punch has been advanced to obtain a donor specimen sample.

FIG. 3 is a schematic, perspective view of a recipient black into which the donor specimen has been placed.

FIGS. 4–8 illustrate steps in the preparation of thin section arrays from the recipient block.

FIG. 10A is a view of an H&E stained, thin section tissue array mounted on a slide for microscopic examination.

FIG. 10B is a magnified view of a portion of the slide in FIG. 10A, showing results of erbB2 mRNA in situ hybridzation on a tissue array from the region in the small rectangle in FIG. 10A.

FIG. 10C is an electrophoresis gel showing that high molecular weight DNA and RNA can be extracted from the breast cancer specimens.

FIG. 10D is an enlarged view of one of the tissue samples of the array in FIG. 10A, showing an immunoperoxidase stain for the erbB2 antigen.

FIG. 10E is a view similar to FIG. 10D, showing high level erbB2 gene amplification detected by fluorescent in situ hybridization (FISH) of tissue in the array by an erbB2 DNA probe.

FIG. 18 is an enlarged view of the donor punch aligned above a structure of interest in the donor block, which is shown in cross-section.

FIG. 19 is an enlarged cross-sectional view of the recipient punch, while

FIG. 20 is a similar view of the donor punch, illustrating the relative cross-sectional diameters of the two punches.

FIG. 21 is a cross-sectional view of the recipient block with the donor specimens arranged in the recipient array, and with lines of microtome sections of the recipient block being shown.

DETAILED DESCRIPTION

Embodiment of FIGS. 1–10

Figure 9:
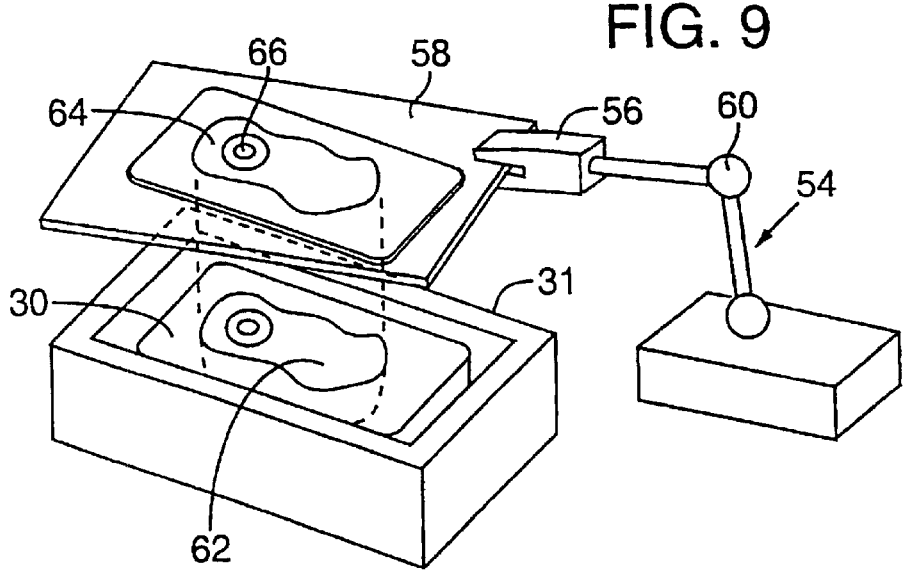
FIG. 9 is a perspective view of a locking device for holding a slide mounted specimen above the tissue in the donor block to locate a region of interest.

A first embodiment of a device for making the microarrays of the present invention is shown in FIGS. 1–2, in which a donor block 30 is shown in a rectangular container 31 mounted on a stationary platform 32 having an L-shaped edge guide 34 that maintains donor container 31 in a predetermined orientation on platform 32. A punch apparatus 38 is mounted above platform 32, and includes a vertical guide plate 40 and a horizontal positioning plate 42. The positioning plate 42 is mounted on an x-y stage (not shown) that can be precisely positioned with a pair of digital micrometers.

Vertical guide plate 40 has a flat front face that provides a precision guide surface against which a reciprocal punch base 44 can slide along a track 46 between a retracted position shown in FIG. 1 and an extended position shown in FIG. 2. An elastic band 48 helps control the movement of base 44 along this path, and the limits of advancement and retraction of base 44 are set by track member 46, which forms a stop that limits the amplitude of oscillation of base 44. A thin wall stainless steel tube punch 50 with sharpened leading edges is mounted on the flat bottom face of base 44, so that punch 50 can be advanced and retracted with respect to platform 32, and the container 31 on the platform. The hollow interior of punch 50 is continuous with a cylindrical bore through base 44, and the bore opens at opening Si on a horizontal lip 53 of base 44.

FIG. 1 shows that a thin section of tissue can be obtained from donor block 30 and mounted on a slide 52 (with appropriate preparation and staining) so that anatomic and microanatomic structures of interest can be located in the block 30. Slide 52 can be held above donor block 30 by an articulated arm holder 54 (FIG. 9) with a clamp 56 which securely holds an edge of a transparent support slide 58. Arm holder 54 can articulate at joint 60, to swivel between a first position in which support slide 58 is locked in position above container 31, and a second position in which support slide 58 moves horizontally out of the position shown in FIG. 9 to permit free access to punch 50.

In operation, the rectangular container 31 is placed on platform 32 (FIG. 1) with edges of container 31 abutting edge guides 34 to hold container 31 in a selected position. A donor block 30 is prepared by embedding a gross tissue specimen (such as a three dimensional tumor specimen 62) in paraffin. A thin section of donor block 30 is shaved off, stained, and mounted on slide 52 as thin section 64, and slide 52 is then placed on support slide 58 and positioned above donor block 30 as shown in FIG. 9. Slide 52 can be moved around on support slide 58 until the edges of thin section 64 are aligned with the edges of the gross pathological specimen 62, as shown by the dotted lines in FIG. 9. Arm 54 is then locked in the first position, to which the arm can subsequently return after displacement to a second position.

A micro-anatomic or histologic structure of interest 66 can then be located by examining the thin section through a microscope (not shown). If the tissue specimen is, for example, an adenocarcinoma of the breast, then the location of interest 66 may be an area of the specimen in which the cellular architecture is suggestive of metaplasia (e.g. pyknotic nuclei, pleomorphism, invasiveness). Once the structure of interest 66 is located, the corresponding region of tissue specimen 62 from which the thin section structure of interest 66 was obtained is located immediately below the structure of interest 66. As shown in FIG. 1, positioning plate 42 can be moved in the x and y directions (under the control of the digital micrometers or a joystick), or the donor block can be moved for larger distances, to align punch 50 in position above the region of interest of the donor block 30, and the support slide 58 is then horizontally pivoted away from its position above donor block 30 around pivot joint 60 (FIG. 9).

Punch 50 is then introduced into the structure of interest in donor block 30 (FIG. 2) by advancing vertical guide plate 40 along track 46 until plate 44 reaches its stop position (which is preset by apparatus 38). As punch 50 advances, its sharp leading edge bores a cylindrical tissue specimen out of the donor block 30, and the specimen is retained within the punch as the punch reciprocates back to its retracted position shown in FIG. 1. The cylindrical tissue specimen can subsequently be dislodged from punch 50 by advancing a stylet (not shown) into opening 51. The tissue specimen is, for example, dislodged from punch 50 and introduced into a cylindrical receptacle of complementary shape and size in an array of receptacles in a recipient block 70 shown in FIG. 3.

One or more recipient blocks 70 can be prepared prior to obtaining the tissue specimen from the donor block 30. Block 70 can be prepared by placing a solid paraffin block in container 31 and using punch 50 to make cylindrical punches in block 70 in a regular pattern that produces an array of cylindrical receptacles of the type shown in FIG. 3. The regular array can be generated by positioning punch 50 at a starting point above block 70 (for example a corner of the prospective array), advancing and then retracting punch 50 to remove a cylindrical core from a specific coordinate on block 70, then dislodging the core from the punch by introducing a stylet into opening 51. The punch apparatus or the recipient block is then moved in a regular increments in the x and/or y directions, to the next coordinate of the array, and the punching step is repeated. In the specific disclosed embodiment of FIG. 3, the cylindrical receptacles of the array have diameters of about 0.6 mm, with the centers of the cylinders being spaced by a distance of about 0.7 mm (so that there is a distance of about 0.05 mm between the adjacent edges of the receptacles).

In a specific example, core tissue biopsies having a diameter of 0.6 mm and a height of 3–4 mm, were taken from selected representative regions of individual "donor" paraffin-embedded tumor blocks and precisely arrayed into a new "recipient" paraffin block (20 mm×45 mm). H&E-stained sections were positioned above the donor blocks and used to guide sampling from morphologically representative sites in the tumors. Although the diameter of the biopsy punch can be varied, 0.6 mm cylinders have been found to be suitable because they are large enough to evaluate histological patterns in each element of the tumor array, yet are sufficiently small to cause only minimal damage to the original donor tissue blocks, and to isolate reasonably homogenous tissue blocks. Up to 1000 such tissue cylinders can be placed in one 20×45 mm recipient paraffin block. Specific disclosed diameters of the cylinders are 0.1–4.0 mm, for example 0.5–2.0 mm, and most specifically less than 1 mm, for example 0.6 mm. Automation of the procedure, with computer guided placement of the specimens, allows very small specimens to be placed tightly together in the recipient array.

FIG. 4 shows the array in the recipient block after the receptacles of the array have been filled with tissue specimen cylinders. The top surface of the recipient block is then covered with an adhesive film 74 from an adhesive coated tape sectioning system (Instrumedics) to help maintain the tissue cylinder sections in place in the array once it is cut With the adhesive film in place, a 4–8 µm section of the recipient block is cut transverse to the longitudinal axis of the tissue cylinders (FIG. 5) to produce a thin microarray section 76 (containing tissue specimen cylinder sections in the form of disks) that is transferred to a conventional specimen slide 78. The microarray section 76 is adhered to slide 78, for example by adhesive on the slide. The film 74 is then peeled away from the underlying microarray member 76 to expose it for processing. A darkened edge 80 of slide 78 is suitable for labeling or handling the slide.

A breast cancer tissue specimen was fixed in cold ethanol to help preserve high-molecular weight DNA and RNA, and 372 of the specimens were fixed in this manner. At least 200 consecutive 4–8 µm tumor array sections can be cut from each block providing targets for correlated in situ analyses of copy number or expression of multiple genes. This analysis is performed by testing for different gene amplifications in separate array sections, and comparing the results of the tests at identical coordinates of the array (which correspond to tissue specimens from the same tissue cylinder obtained from donor block). This approach enables measurement of virtually hundreds of molecular characteristics from every tumor, thereby facilitating construction of a large series of correlated genotypic or phenotypic characteristics of uncultured human tumors.

An example of a single microarray 76 containing 645 specimens is shown in FIG. 10A. An enlarged section of the microarray (highlighted by a rectangle in FIG. 10A) is shown in FIG. 10B, in which an autoradiogram of erbB2 mRNA in situ hybridization illustrates that two adjacent specimens in the array demonstrate a strong hybridization signal. FIG. 10C illustrates electrophoresis gels which demonstrate that high molecular weight DNA and RNA can be extracted from breast cancer specimens fixed in ethanol at 4° C. overnight in a vacuum oven.

One of the tissue specimens that gave the fluorescent "positive" signals was also analyzed by immunoperoxidase staining, as shown in FIG. 10D, where it was confirmed (by the dark stain) that the erbB2 gene product was present. A DNA probe for the erbB2 gene was used to perform fluorescent in situ hybridization (FISH). FIG. 10D shows one of the tumor array elements, which demonstrated high level erbB2 gene amplification. The insert in FIG. 10E shows three nuclei with numerous tightly clustered erbB2 hybridization signals and two copies of the centromeric reference probe. Additional details about these assays are given in Examples 1–4 below.

Figure 11:
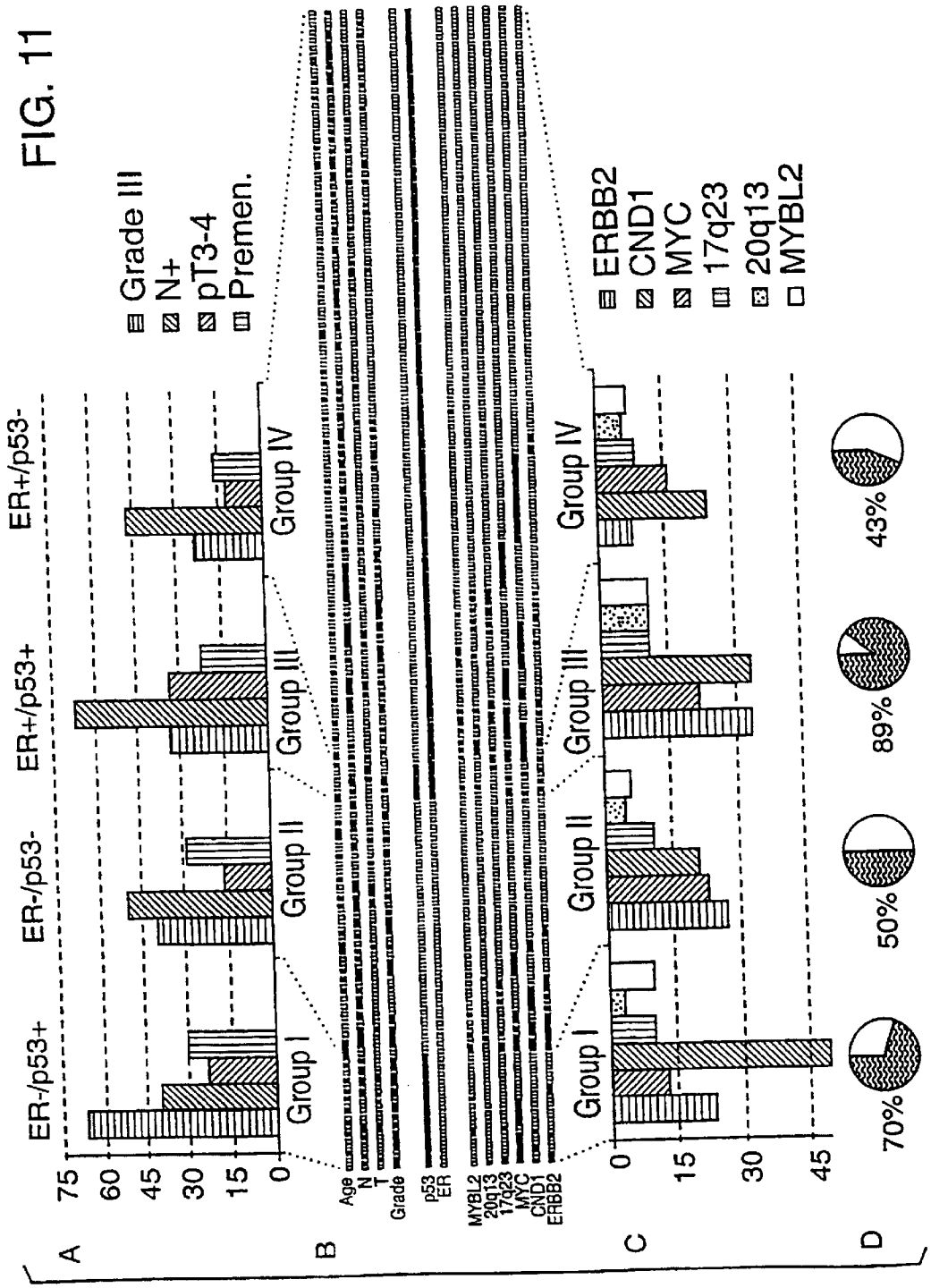
FIG. 11 is a schematic view illustrating an example of parallel analysis of arrays obtained by the method of the present invention.

The potential of the array technology of the present invention to perform rapid parallel molecular analysis of multiple tissue specimens is illustrated in FIG. 11, where the y-axis of the graphs corresponds to percentages of tumors in specific groups that have defined clinicopathological or molecular characteristics. This diagram shows correlations between clinical and histopathological characteristics of the tissue specimens in the micro-array. Each small box in the aligned rows of FIG. 11B represents a coordinate location in the array. Corresponding coordinates of consecutive thin sections of the recipient block are vertically aligned above one another in the horizontally extending rows. These results show that the tissue specimens could be classified into four classifications of tumors (FIG. 11A) based on the presence or absence of cell membrane estrogen receptor expression, and the presence or absence of the p53 mutation in the cellular DNA. In FIG. 11B, the presence of the p53 mutation is shown by a darkened box, while the presence of estrogen receptors is also shown by a darkened box. Categorization into each of four groups (ER−/p53+, ER−/p53−, ER+/p53+ and ER+/p53−) is shown by the dotted lines between FIGS. 11A and 11B, which divide the categories into Groups I, II, III and IV corresponding to the ER/p53 status.

FIG. 11B also shows clinical characteristics that were associated with the tissue at each respective coordinate of the array. A darkened box for Age indicates that the patient is premenopausal, a darkened box N indicates the presence of metastatic disease in the regional lymph nodes, a darkened box T indicates a stage 3 or 4 tumor which is more clinically advanced, and a darkened box for grade indicates a high grade (at least grade III) tumor, which is associated with increased malignancy. The correlation of ER/p53 status can be performed by comparing the top four lines of clinical indicator boxes (Age, N, T, Grade) with the middle two lines of boxes (ER/p53 status). The results of this cross correlation are shown in the bar graph of FIG. 11A, where it can be seen that ER−/p53+ (Group I) tumors tend to be of higher grade than the other tumors, and had a particularly high frequency of myc amplification, while ER+/p53+ (Group III) tumors were more likely to have positive nodes at the time of surgical resection. The ER−/p53− (Group II) showed that the most common gene amplified in that group was erbB2. ER−/p53− (Group II) and ER+/p53− (Group IV) tumors, in contrast, were shown to have fewer indicators of severe disease, thus suggesting a correlation between the absence of the p53 mutation and a better prognosis.

This method was also used to analyze the copy numbers of several other major breast cancer oncogenes in the 372 arrayed primary breast cancer specimens in consecutive FISH experiments, and those results were used to ascertain correlations between the ER/p53 classifications and the expression of these other oncogenes. These results were obtained by using probes for each of the separate oncogenes, in successive sections of the recipient block. and comparing the results at corresponding coordinates of the array. In FIG. 11B, a positive result for the amplification of the specific oncogene or marker (mybL2, 20q13, 17q23, myc, cnd1 and erbB2) is indicated by a darkened box. The erbB2 oncogene was amplified in 18% of the 372 arrayed specimens, myc in 25% and cyclin D1 (cnd1) in 24% of the tumors.

The two recently discovered novel regions of frequent DNA amplification in breast cancer, 17q23 and 20q13, were found to be amplified in 13% and 6% of the tumors, respectively. The oncogene mybL2 (which was recently localized to 20q13.1 and found to be overexpressed in breast cancer cell lines) was found to be amplified in 7% of the same set of tumors. MybL2 was amplified in tumors with normal copy number of the main 20q13 locus, indicating that it may define an independently selected region of amplification at 20q. Dotted lines between FIGS. 11B and 11C again divide the complex co-amplification patterns of these genes into Groups I–IV which correspond to ER−/p53+, ER−/p53−, ER+/p53+ and ER+/p53−.

FIGS. 11C and 11D show that 70% of the ER−/p53+ specimens were positive for one or more of these oncogenes, and that myc was the predominant oncogene amplified in this group. In contrast, only 43% of the specimens in the ER+/p53− group showed co-amplification of one of these oncogenes, and this information could in turn be correlated with the clinical parameters shown in FIG. 11A. Hence the microarray technology permits a large number of tumor specimens to be conveniently and rapidly screened for these many characteristics, and analyzed for patterns of gene expression that may be related to the clinical presentation of the patient and the molecular evolution of the disease. In the absence of the microarray technology of the present invention, these correlations are more difficult to obtain.

Figure 12:
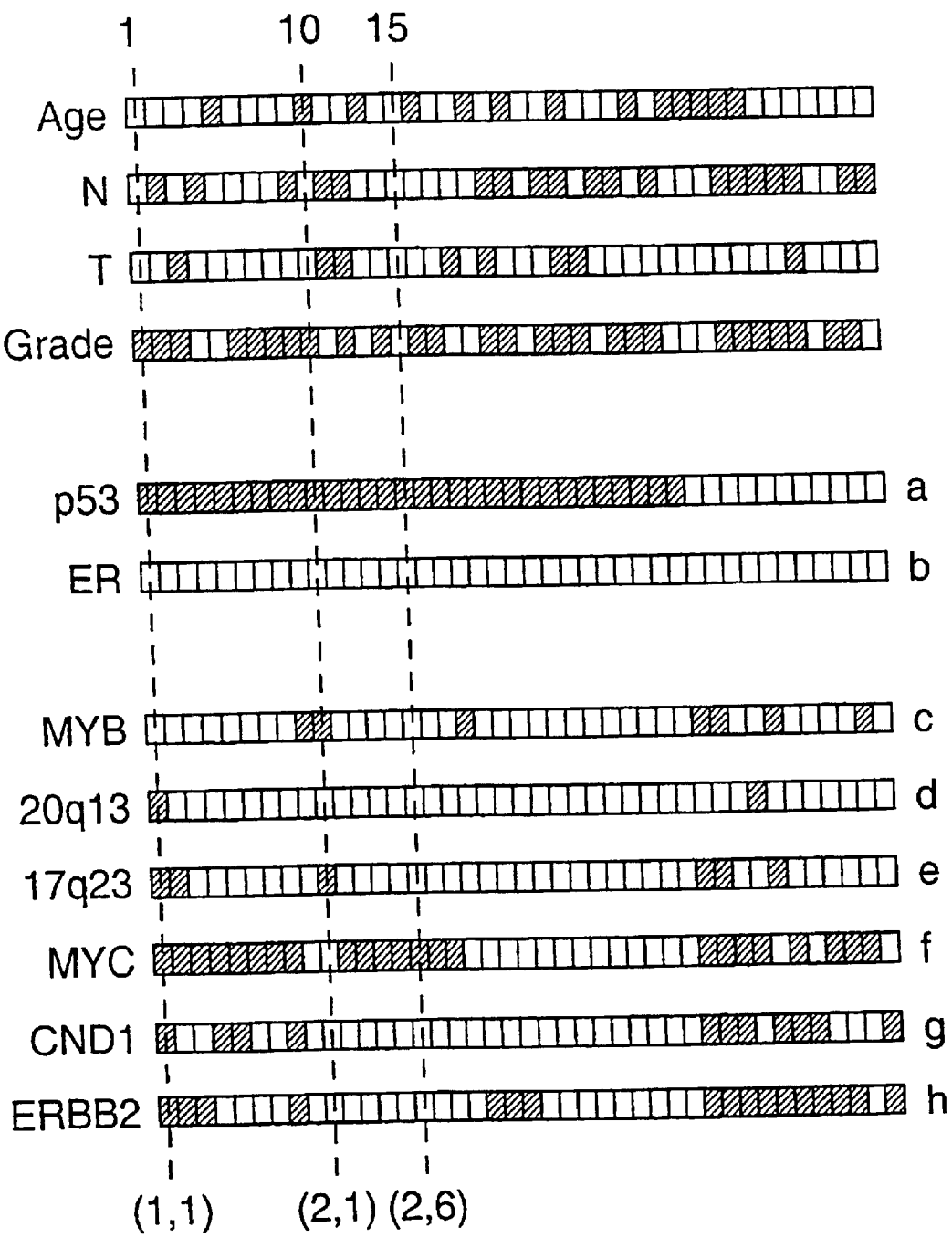
FIG. 12 is an enlarged view of a portion of FIG. 11.
Figure 13:
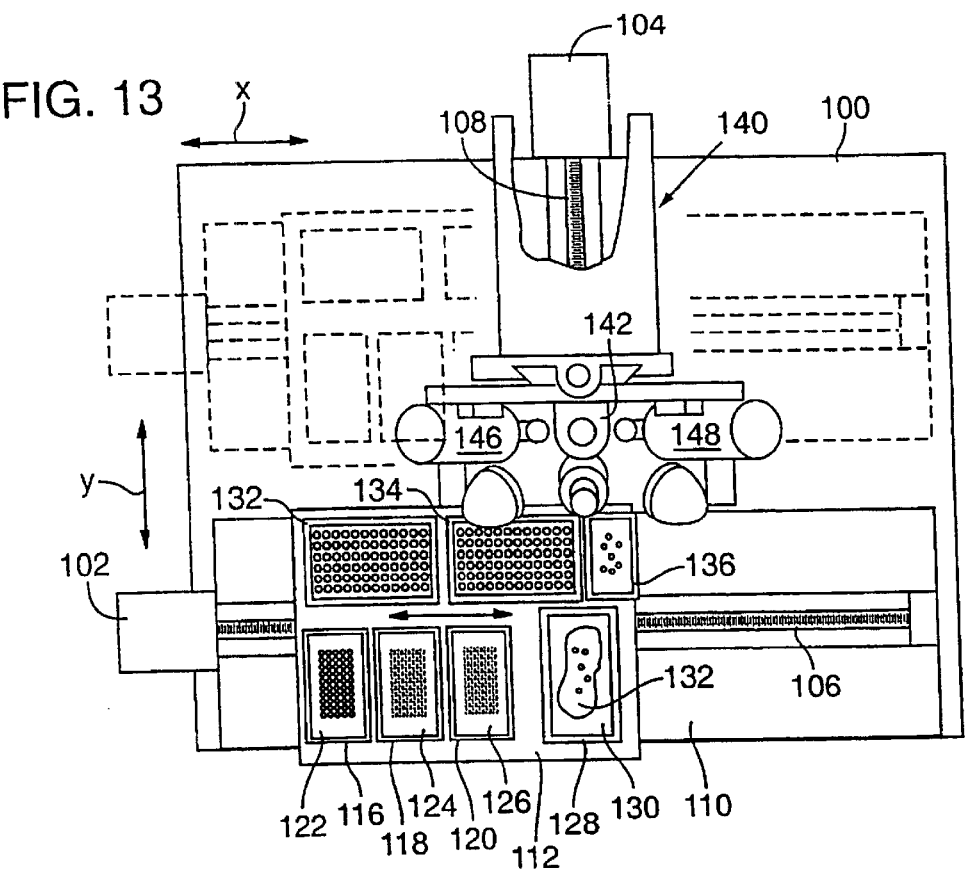
FIG. 13 is a top view of a second embodiment of a device for forming the arrays of the present invention.
Figure 14:
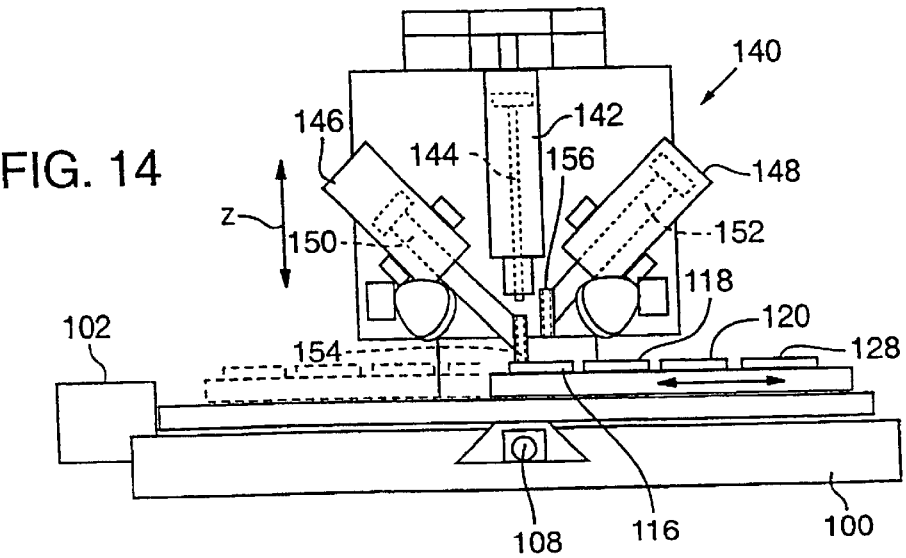
FIG. 14 is a front view of the device shown in FIG. 13, illustrating the formation of a receptacle in a recipient block with a recipient punch.
Figure 15:
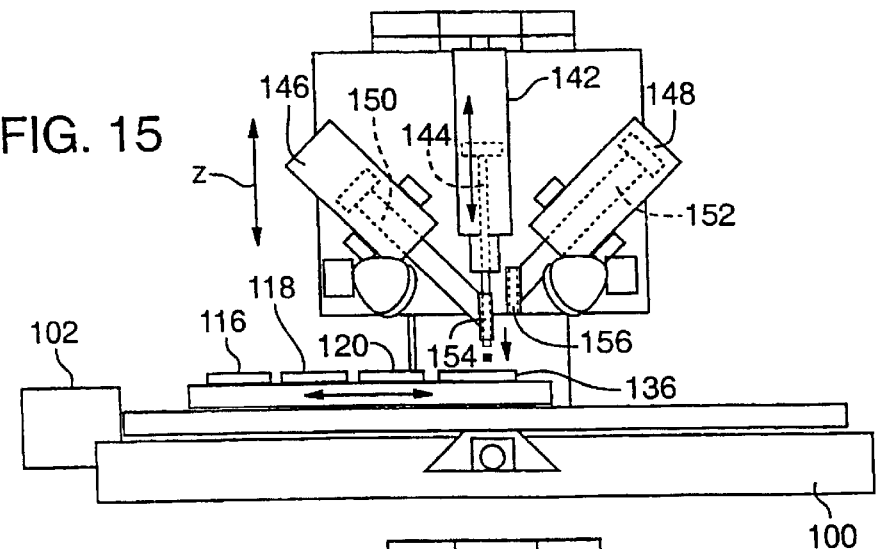
FIG. 15 is a view similar to FIG. 14, but showing expulsion of a plug from the recipient punch into a discard tray.
Figure 16:
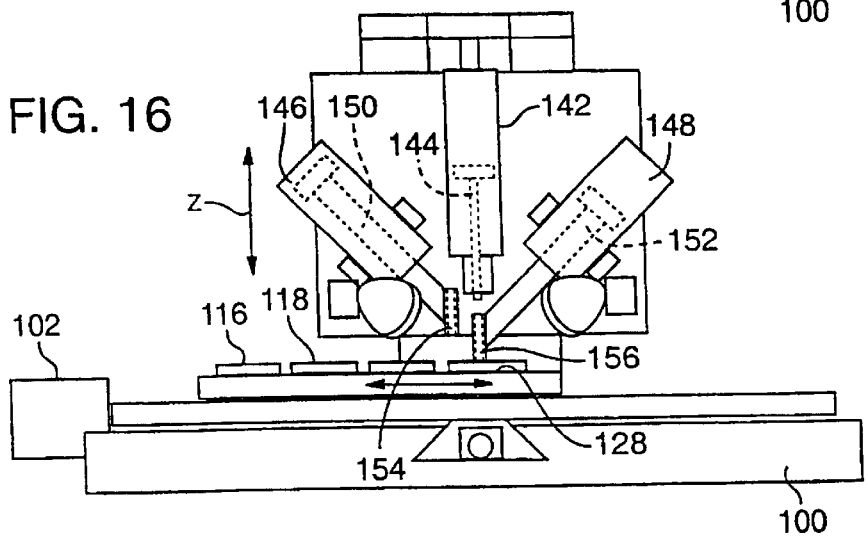
FIG. 16 is a view showing a donor punch obtaining a tissue specimen from a donor block.
Figure 17:
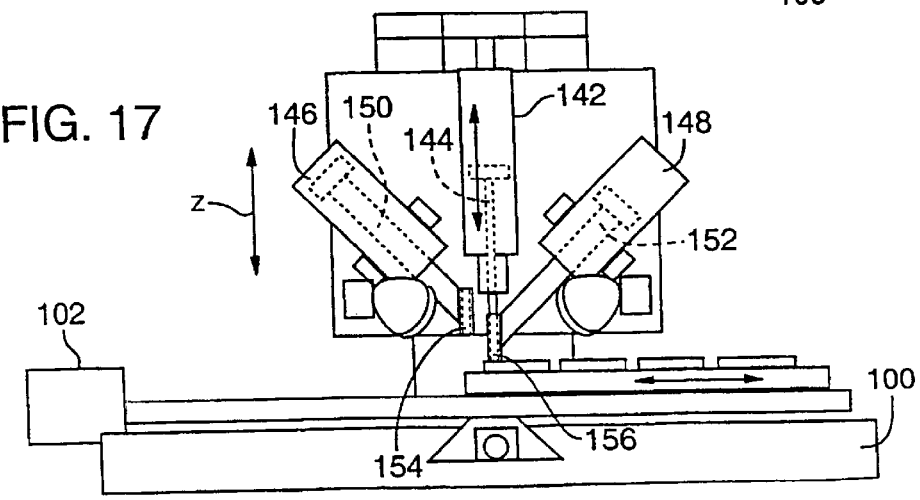
FIG. 17 is a view showing insertion of the donor tissue into a receptacle of the recipient block.

A specific method of obtaining these correlations is illustrated in FIG. 12, which is an enlargement of the right hand portion of FIG. 11B. The microarray 76 (FIG. 10A) is arranged in sections that contain seventeen rows and nine columns of circular locations that correspond to cross-sections of cylindrical tissue specimens from different tumors, wherein each location in the microarray can be represented by the coordinates (row, column). For example, the specimens in the first row of the first section have coordinate positions (1,1), (1,2) . . . (1,9), and the specimens in the second row have coordinate positions (2,1), (2,2) . . . (2,9). Each of these array coordinates can be used to locate tissue specimens from corresponding positions on sequential sections of the recipient block, to identify tissue specimens of the array that were cut from the same tissue cylinder.

As shown in FIG. 12, the rectangular array is converted into a linear representation in which each box of the linear representation corresponds to a coordinate position of the array. Each of the lines of boxes is aligned so that each box that corresponds to an identical array coordinate position is located above other boxes from the same coordinate position. Hence the boxes connected by dotted line 1 correspond to the results that can be obtained by looking at the results at coordinate position (1,1) in successive thin sections of the donor block, or clinical data that may not have been obtained from the microarray, but which can be entered into the system to further identify tissue from a tumor that corresponds to that coordinate position. Similarly, the boxes connected by dotted line 10 correspond to the results that can be found at coordinate position (2,1) of the array, and the boxes connected by dotted line 15 correspond to the results at coordinate position (2,6) of the array. The letters a, b, c, d, e, f, g, and h correspond to successive sections of the donor block that are cut to form the array.

By comparing the aligned boxes along line 1 in FIG. 12, it can be seen that a tumor was obtained from a postmenopausal woman with no metastatic disease in her lymph nodes at the time of surgical resection, in which the tumor was less than stage 3, but in which the histology of the tumor was at least Grade III. A tissue block was taken from this tumor and introduced into the recipient array at coordinate position (1,1), and once the array was completed it was sectioned into eight parallel sections (a, b, c, d, e, f, g, and h) each of which contained a representative section of the cylindrical array. Each of these sections was analyzed with a different probe specific for a particular molecular attribute. In section a, the results indicated that this tissue specimen was p53+; in section b that it was ER−; in section c that it did not show amplification of the mybL2 oncogene; in separate sections d, e, f, g and h that it was positive for the amplification of 20q13, 17q23, myc, cnd1 and erbB2.

Similar comparisons of molecular characteristics of the tumor specimen cylinder that was placed at coordinate position (2,1) can be made by following vertical line 10 in FIG. 12, which connects the tenth box in each line, and corresponds to the second row, first column (2,1) of the array 76 in FIG. 10(A). Similarly the characteristics of the sections of the tumor specimen cylinder at coordinate position (2,6) can be analyzed by following vertical line 15 down through the 15$^{th}$ box of each row. In this manner, parallel information about the separate sections of the array can be performed for all 372 positions of the array. This information can be presented visually for analysis as in FIG. 12, or entered into a database for analysis and correlation of different molecular characteristics (such as patterns of oncogene amplification, and the correspondence of those patterns of amplification to clinical presentation of the tumor).

Analysis of consecutive sections from the arrays enables co-localization of hundreds of different DNA, RNA or protein targets in the same cell populations in morphologically defined regions of every tumor, which facilitates construction of a database of a large number of correlated genotypic or phenotypic characteristics of uncultured human tumors. Scoring of mRNA in situ hybridizations or protein immunohistochemical staining is also facilitated with tumor tissue microarrays, because small amounts of the identical reagents are used for each analysis. The tumor arrays also substantially reduce tissue consumption, reagent use, and workload when compared with processing individual conventional specimens for sectioning, staining and scoring. The combined analysis of several DNA, RNA and protein targets provides a powerful means for stratification of tumor specimens by virtue of their molecular characteristics. Such patterns will be helpful to detect previously unappreciated but important molecular features of the tumors that may turn out to have diagnostic or prognostic utility.

These results show that the very small cylinders used to prepare tissue arrays can in most cases provide accurate information, especially when the site for tissue sampling from the donor block is selected to contain histological structures that are most representative of tumor regions. It is also possible to collect samples from multiple histologically defined regions in a single donor tissue block to obtain a more comprehensive representation of the original tissue, and to directly analyze the correlation between phenotype (tissue morphology) and genotype. For example, an array could be constructed to include hundreds of tissues representing different stages of breast cancer progression (e.g. normal tissue, hyperplasia, atypical hyperplasia, intraductal cancer, invasive and metastatic cancer). The tissue array technology would then be used to analyze the molecular events that correspond to tumor progression.

A tighter packing of cylinders and a larger recipient block can also provide an even higher number of specimens per array. Entire archives from pathology laboratories could be placed in replicate 1000 specimen tissue microarrays for molecular profiling. Using automation of the procedure for sampling and arraying, it is possible to make dozens of replicate tumor arrays, each providing hundreds of sections for molecular analyses. The same strategy and instrumentation developed for tumor arrays also enables microdissection of tissue cylinders for isolation of high-molecular weight RNA and DNA from optimally fixed, morphologically defined tumor tissue elements, thereby allowing correlated analysis of the same tumors by PCR-based techniques for RNA and DNA. When nucleic acid analysis is planned, the tissue specimen is preferably fixed (before embedding in paraffin) in ethanol or Molecular Biology Fixative (Streck Laboratories, Inc., Omaha, Nebr.) instead of in formalin, because formalin can cross-link and otherwise damage nucleic acid. The tissue cylinder of the present invention provides an ample amount of DNA or RNA on which to perform a variety of molecular analyses.

The potential of this array technology has been illustrated in FISH analysis of gene amplifications in breast cancer. FISH is an excellent method for visualization and accurate detection of genetic rearrangements (amplifications, deletions or translocations) in individual, morphologically defined cells. The combined tumor array technology allows FISH to become a powerful, high-throughput method that permits the analysis of hundreds of specimens per day.

Embodiment of FIGS. 13–23

An example of an automated system for high speed preparation of the microarrays is shown in FIGS. 13–23. The system includes a stage 100 having an x drive 102 and a y drive 104, each of which respectively rotates a drive shaft 106, 108. The shaft 108 moves a specimen bench 110 in a y direction, while the shaft 106 moves a tray 112 on the bench 110 in an x direction. Mounted in a front row of tray 112 are three recipient containers 116, 118 and 120, each of which contains a recipient paraffin block 122, 124 or 126, and a donor container 128 that contains a donor paraffin block 130, in which is embedded a tissue specimen 132. In a back row on the tray are two multi-well donor trays 132, 134 (which contain multiple containers for maintaining specimens in liquid medium), and a discard container 136.

Disposed above stage 100 is a punch apparatus 140 that can move up and down in a z direction. Apparatus 140 includes a central, vertically disposed, stylet drive 142 in which reciprocates a stylet 144. Apparatus 140 also includes an inclined recipient punch drive 146, and a inclined donor punch drive 148. Punch drive 146 includes a reciprocal ram 150 that carries a tubular recipient punch 154 at its distal end, and punch drive 148 includes a reciprocal ram 152 that carries a donor tubular punch 156 at its distal end. When the ram 150 is extended (FIG. 14), recipient punch 154 is positioned with the open top of its tubular bore aligned with stylet 144, and when ram 152 is extended (FIG. 16), donor punch 156 is positioned with the open top of its tubular bore aligned with stylet 144.

The sequential operation of the apparatus 140 is shown in FIGS. 13–17. Once the device is assembled as in FIG. 13, a computer system can be used to operate the apparatus to achieve high efficiency. Hence the computer system can initialize itself by determining the location of the containers on tray 112 shown in FIG. 13. The x and y drives 102, 104 are then activated to move bench 110 and tray 112 to the position shown in FIG. 14, so that activation of ram 150 extends recipient punch 154 to a position above position (1,1) in the recipient block 122. Once punch 154 is in position, apparatus moves downward in the z direction to punch a cylindrical bore in the paraffin of the recipient block. The apparatus 140 then moves upwardly in the z direction to raise punch 154 out of the paraffin recipient block 122, but the punch 154 retains a core of paraffin that leaves a cylindrical receptacle in the recipient block 122. The x-y drives are then activated to move bench 110 and position discard container 136 below punch 154. Stylet drive 142 is then activated to advance stylet 144 into the open top of the aligned punch 154, to dislodge the paraffin core from punch 154 and into discard container 136.

Stylet 144 is retracted from recipient punch 154, ram 150 is retracted, and the x-y drive moves bench 110 and tray 112 to place donor container 128 is a position (shown in FIG. 16) such that advancement of ram 152 advances donor punch 156 to a desired location over the donor block 130. Apparatus 140 is then moved down in the z direction to punch a cylindrical core of tissue out of the donor block 130, and apparatus 140 is then moved in the z direction to withdraw donor punch 156, with the cylindrical tissue specimen retained in the punch. The x-y drive then moves bench 110 and tray 112 to the position shown in FIG. 17, such that movement of apparatus 140 downwardly in the z direction advances donor punch 156 into the receptacle at the coordinate position (1,1) in block 122 from which the recipient plug has been removed. Donor punch 156 is aligned below stylet 144, and the stylet is advanced to dislodge the retained tissue cylinder from donor punch 156, so that the donor tissue cylinder remains in the receptacle of the recipient block 122 as the apparatus 140 moves up in the z direction to retract donor punch 156 from the recipient array. Ram 152 is then retracted.

This process can be repeated until a desired number of recipient receptacles have been formed and filled with cylindrical donor tissues at the desired coordinate locations of the array. Although this illustrated method shows sequential alternating formation of each receptacle, and introduction of the tissue cylinder into the formed receptacle, it is also possible to form all the receptacles in recipient blocks 122, 124 and 126 as an initial step, and then move to the step of obtaining the tissue specimens and introducing them into the preformed receptacles. The same tissue specimen 132 can be repeatedly used, or the specimen 132 can be changed after each donor tissue specimen is obtained, by introducing a new donor block 130 into container 128. If the donor block 130 is changed after each tissue cylinder is obtained, each coordinate of the array can include tissue from a different tissue specimen.

A positioning device is shown in FIG. 18, which helps locate structures of interest from which donor specimens can be taken. The positioning device includes a support slide 160 that extends between opposing walls of donor container 128, to support a specimen slide 162 on which is mounted a thin stained section of the specimen 132 in donor block 130. Using a microscope mounted on apparatus 140 (the objective of the microscope is shown at 166), microanatomic structures of interest can be found. The correct vertical height of apparatus 140 above the top surface of donor block 130 can be determined by the use of two positioning lights 168, 170 that am mounted to apparatus 140. Light beams 172, 174 are projected from lights 168, 170 at an angle such that the beams coincide at a single spot 176 when vertical height of apparatus 140 above the top surface of the light is at a desired z level. This desired z level will position the punches 152, 154 at an appropriate height to penetrate the surface of block 130 at the desired location, and to a desired depth.

It is advantageous if the tissue cylinders punched from block 130 fit securely in the recipient receptacles that are formed to receive them. If the donor punch 156 has the same inner and outer diameters as the recipient punch 154, then the cylindrical donor tissue specimen will be formed by the inner diameter of the punch, and the recipient receptacle will be formed by the outer diameter of the punch. This discrepancy will provide a receptacle that is slightly larger in diameter than the donor tissue cylinder. Hence, as shown in FIGS. 19 and 20, the recipient punch 154 preferably has a smaller diameter than the donor punch 156. Recipient punch will therefore form a cylindrical receptacle (having a diameter corresponding to the outer diameter of punch 154) that is substantially the same diameter as the tissue specimen cylinder 180, which is formed with a diameter that is determined by the inner diameter of the donor punch 156.

FIG. 21 illustrates a cross-section through the recipient array, once the receptacles 182 have been formed and filled with tissue specimen cylinders 180. Small partitions of paraffin material 122 separate tissue cylinders 18, and the receptacles 182 as illustrated are deeper than the specimen cylinders 180, such that a small clearance is present between the specimen and the bottom of the receptacles. Once the array has been formed, a microtome can be used to cut a thin section S off the top of the block 122, so that the section S can be mounted on a specimen slide 162 (FIG. 18) to help locate structures of interest in the tissue specimen 132. The microtome then also cuts thin parallel sections a, b, c, d, e, f, g, and h that can each be subjected to a different molecular analysis, as already described.

Exemplary Operating Environment

Figure 22:
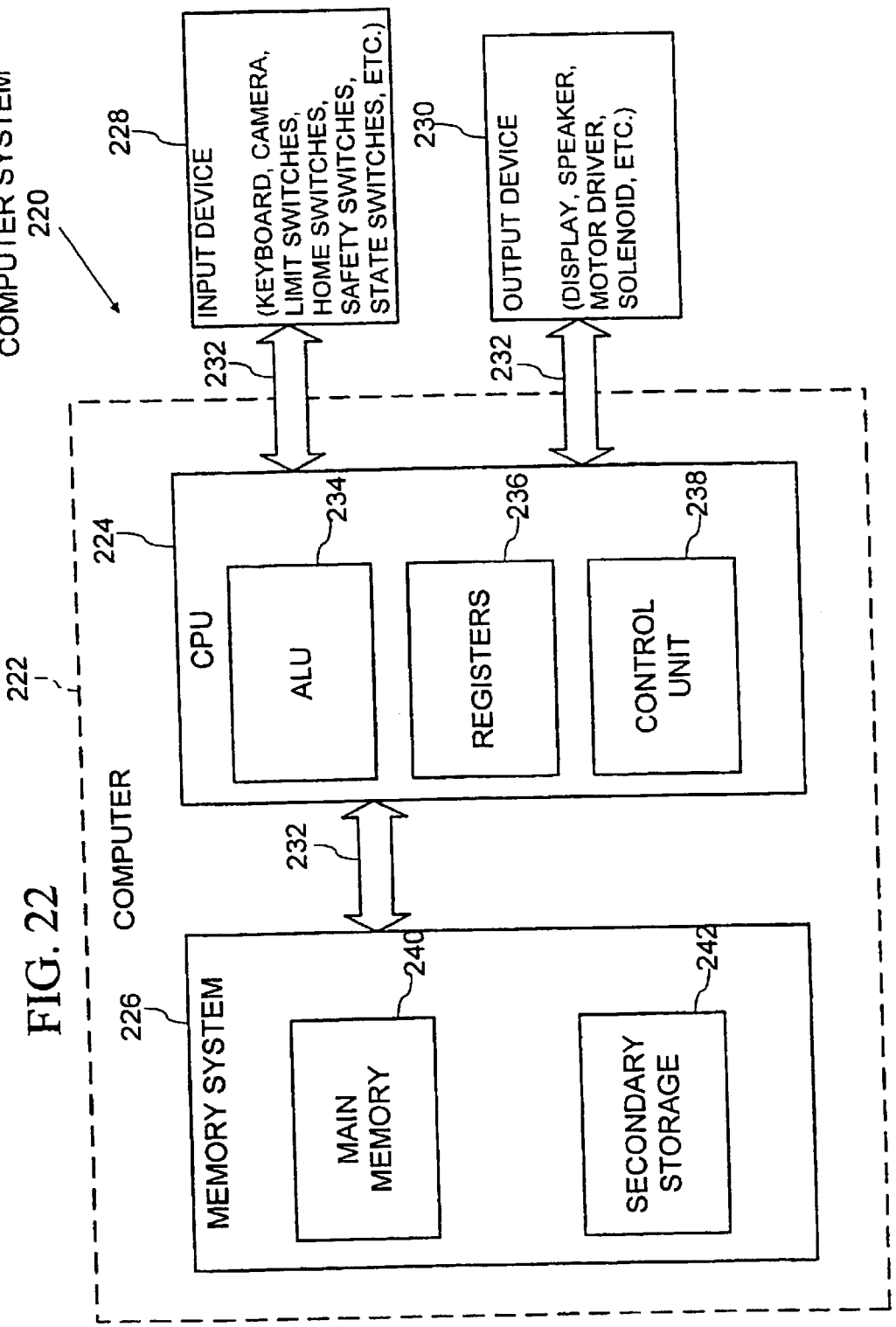
FIG. 22 is a schematic view of a computer system in which the method of the present invention can be implemented.

FIG. 22 and the following discussion are intended to provide a brief, general description of a suitable computing environment in which the invention may be implemented. The invention is implemented in a variety of program modules. Generally, program modules include routines, programs, components, data structures, ect. that perform particular tasks or implement particular abstract data types. The invention may be practiced with other computer system configurations, including hand-held devices, multiprocessor systems, microprocessor-based or programmable consumer electronics, minicomputers, mainframe computers, and the like. The invention may also be practiced in distributed computing environments where tasks are performed by remote processing devices that are linked through a communications network. In a distributed computing environment, program modules may be located in both local and remote memory storage devices.

Referring to FIG. 22, an operating environment for an illustrated embodiment of the present invention is a computer system 220 with a computer 222 that comprises at least one high speed processing unit (CPU) 224, in conjunction with a memory system 226, an input device 228, and an output device 230. These elements are interconnected by at least one bus structure 232.

The illustrated CPU 224 is of familiar design and includes an ALU 234 for performing computations, a collection of registers 236 for temporary storage of data and instructions, and a control unit 238 for controlling operation of the system 220. The CPU 224 may be a processor having any of a variety of architectures including Alpha from Digital; MIPS from MIPS Technology, NEC, IDT, Siemens and others; x 86 from Intel and others, including Cyrix, AMD, and Nexgen; 680 x 0 from Motorola; and PowerPC from IBM and Motorola.

The memory system 226 generally includes high-speed main memory 240 in the form of a medium such as random access memory (RAM) and read only memory (ROM) semiconductor devices, and secondary storage 242 in the form of long term storage mediums such as floppy disks, hard disks, tape, CD-ROM, flash memory, etc. and other devices that store data using electrical, magnetic, optical or other recording media. The main memory 240 also can include video display memory for displaying images through a display device. Those skilled in the art will recognize that the memory 226 can comprise a variety of alternative components having a variety of storage capacities.

The input and output devices 228, 230 also are familiar. The input device 228 can comprise a keyboard, a mouse, a scanner, a camera, a capture card, a limit switch (such as home, safety or state switches), a physical transducer (e.g., a microphone), etc. The output device 230 can comprise a display, a printer, a motor driver, a solenois, a transducer (e.g., a speaker), etc. Some devices, such as a network interface or a modem, can be used as input and/or output devices.

As is familiar to those skilled in the art, the computer system 220 further includes an operating system and at least one application program. The operating system is the set of software which controls the computer system's operation and the allocation of resources. The application program is the set of software that performs a task desired by the user, using computer resources made available through the operating system. Both are resident in the illustrated memory system 226.

For example, the invention could be implemented with a Power Macintosh 8500 available from Apple Computer, or an IBM compatible Personal Computer (PC). The Power Mcintosh uses a PowerPC 604 CPU from Motorola and runs a MacOS operating system from Apple Computer such as System 8. Input and output devices can be interfaced with the CPU using the well-known SCSI interface or with expansion cards using the Peripheral Component Interconnect (PCI) bus. A typical configuration of a Power Macintosh 8500 has 72 megabytes of RAM for high-speed main memory and a 2 gigabyte hard disk for secondary storage. An IBM compatible PC could have a configuration with 32 megabytes of RAM for high-speed main memory and a 2–4 gigabyte hard disk for secondary storage.

In accordance with the practices of persons skilled in the art of computer programming, the present invention is described with reference to acts and symbolic representations of operations that are performed by the computer system 220, unless indicated otherwise. Such acts and operations are sometimes referred to as being computer-executed. It will be appreciated that the acts and symbolically represented operations include the manipulation by the CPU 224 of electrical signals representing data bits which causes a resulting transformation or reduction of the electrical signal representation, and the maintenance of data bits at memory locations in the memory system 226 to thereby reconfigure or otherwise alter the computer system's operation, as well as other processing of signals. The memory locations where data bits are maintained are physical locations that have particular electrical, magnetic, or optical properties corresponding to the data bits.

Description or Computer-Array System

Figure 23:
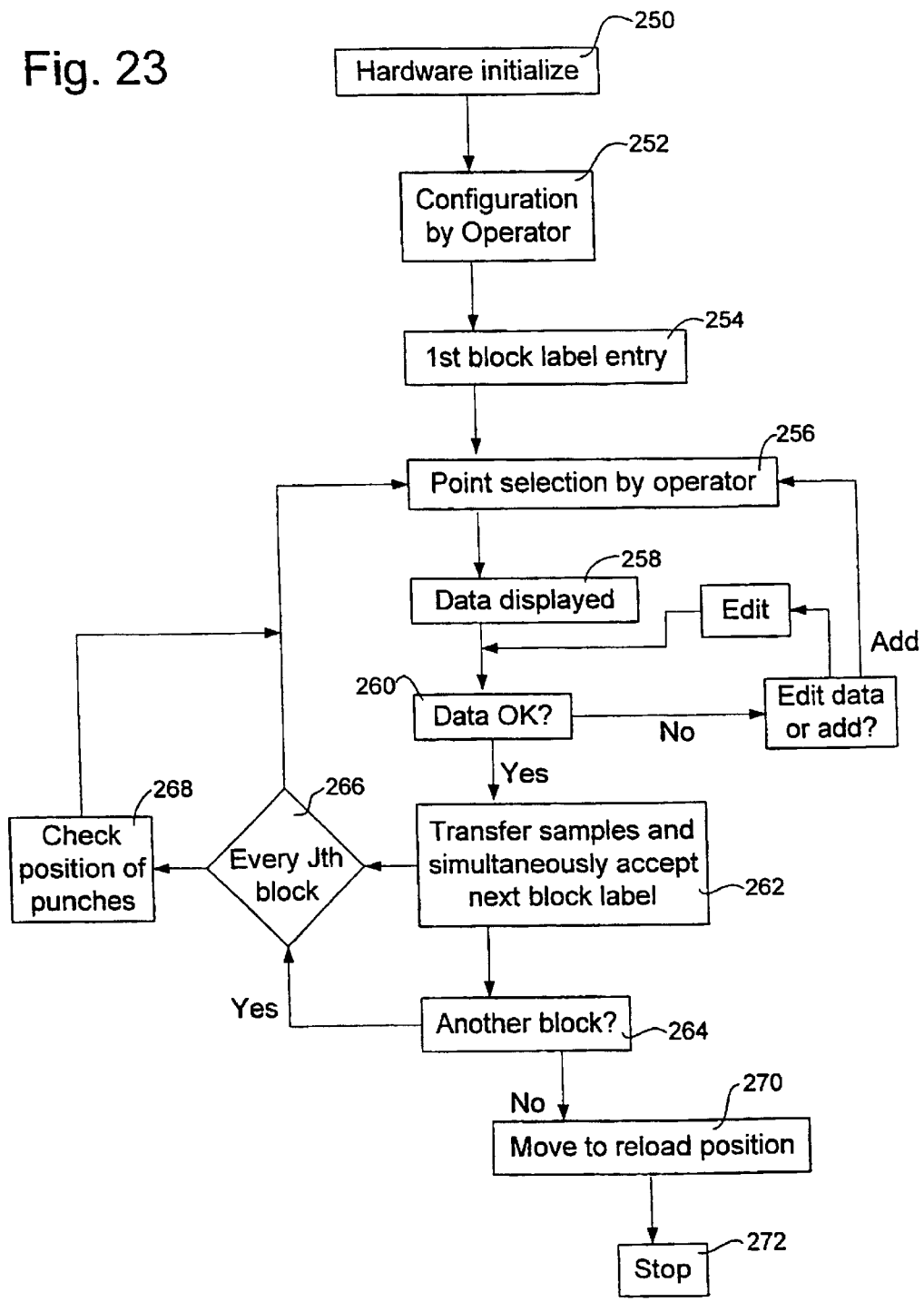
FIG. 23 is an algorithm illustrating an example of the computer implemented method of the present invention.

A block diagram showing a system for carrying out the invention is shown at FIG. 23. The hardware is initialized at step 250, for example by determining the position of the punches 154, 156, bench 110, and tray 112. The system may then be configured by the operator at step 252, for example by entering data or prompting the system to find the location (x, y, z coordinates) of the upper right corner of each recipient block 122–126, as well as the locations of trays 130–136. The number of donor blocks, receptacles, operating speed, etc. may also be entered at this time.

At step 254, the system prompts for entry of identifying information about the first donor block 130 that will be placed in tray 128. This identifying information can include accession number information, clinical information about the specimen, and any/or other information that would be useful in analyzing the tumor arrays. At step 256, the operator pushes a select function button, which raises the punches 154, 156 and enables a joystick to move the specimens using the x-y drives. The entered data is displayed at step 258, and approved at step 260.

The system then obtains one or more donor specimens from the identified donor block at step 262, and prompts the user for entry of information about the next donor block. If information about another block is entered, the system returns to step 256 and obtains the desired number of specimens from the new block. After a new donor block has been placed in donor container 128, the system also checks the position of the punches at step 268. If information about another block is not entered at step 264, the system moves the donor tray to the reloading position to that a block 130 in the donor tray can be removed. This system is also adaptable to sampling cylindrical biopsies from histologically controlled sites of specimens (such as tumors) for DNA/RNA isolation.

The automated tumor array technology easily allows testing of dozens or hundreds of markers from the same set of tumors. These studies can be carried out in a multi-center setting by sending replicate tumor array blocks or sections to other laboratories. The same approach would be particularly valuable for testing newly discovered molecular markers for their diagnostic, prognostic or therapeutic utility. The tissue array technology also facilitates basic cancer research by providing a platform for rapid profiling of hundreds or thousands of tumors at the DNA, RNA and protein levels, leading to a construction of a correlated database of biomarkers from a large collection of tumors. For example, search for amplification target genes requires correlated analyses of amplification and expression of dozens of candidate genes and loci in the same cell populations. Such extensive molecular analyses of a defined large series of tumors would be difficult to carry out with conventional technologies.

Examples of Array Technology

Applications of the tissue array technology are not limited to studies of cancer, although the following Examples 1–4 disclose embodiments of its use in connection with analysis of neoplasms. Array analysis could also be instrumental in understanding expression and dosage of multiple genes in other diseases, as well as in normal human or animal tissues, including repositories of tissues from different transgenic animals or cultured cells. The following specific examples illustrate some particular embodiments of the invention.

EXAMPLE 1

Tissue Specimens

A total of 645 breast cancer specimens were used for construction of a breast cancer tumor tissue microarray. The samples included 372 fresh-frozen ethanol-fixed tumors, as well as 273 formalin-fixed breast cancers, normal tissues and fixation controls. The subset of frozen breast cancer samples was selected at random from the tumor bank of the institute of Pathology, University of Basel, which includes more than 1500 frozen breast cancers obtained by surgical resections during 1986–1997. Only the tumors from this tumor bank were used for molecular analyses. This subset was reviewed by a pathologist, who determined that the specimens included 259 ductal, 52 lobular, 9 medullary, 6 mucinous, 3 cribriform, 3 tubular, 2 papillary, 1 histiocytic, 1 clear cell, and 1 lipid rich carcinoma. There were also 15 ductal carcinomas in situ, 2 carcinosarcomas, 4 primary carcinomas that had received chemotherapy before surgery, 8 recurrent tumors and 6 metastases. Histological grading was only performed in invasive primary tumors that had not undergone previous chemotherapy. Of these tumors, 24% were grade 1, 40%/a grade 2, and 36% grade 3. The pT stage was pT1 in 29%, pT2 in 54%, pT3 in 9%, and pT4 in 8%. Axillary lymph nodes had been examined in 282 patients (45% pN0, 46% pN1, 9% pN2). All previously unfixed tumors were fixed in cold ethanol at +4° C. overnight and then embedded in paraffin.

EXAMPLE 2

Immunohistochemistry

After formation of the array and sectioning of the donor block, standard indirect immunoperoxidase procedures were used for immunohistochemistry (ABC-Elite, Vector Laboratories). Monoclonal antibodies from DAKO (Glostrup, Denmark) were used for detection of p53 (DO-7, mouse, 1:200), erbB-2 (c-erbB-2, rabbit, 1:4000), and estrogen receptor (ER IDS, mouse, 1:400). A microwave pretreatment was performed for p53 (30 minutes at 90°) and erbB-2 antigen (60 minutes at 90°) retrieval. Diaminobenzidine was used as a chromogen. Tumors with known positivity were used as positive controls. The primary antibody was omitted for negative controls. Tumors were considered positive for ER or p53 if an unequivocal nuclear positivity was seen in at least 10% of tumor cells. The erbB-2 staining was subjectively graded into 3 groups: negative (no staining), weakly positive (weak membranous positivity), strongly positive (strong membranous positivity).

EXAMPLE 3

Fluorescent In Situ Hybridization (FISH)

Two-color FISH hybridizations were performed using Spectrumm-Orange labeled cyclin D1, myc or erbB2 probes together with corresponding FITC labeled centromeric reference probes (Vysis). One-color FISH hybridizations were done with spectrum orange-labeled 20q13 minimal common region (Vysis, and see Tanner et al., *Cancer Res.* 54:4257–4260 (1994)), mybL2 and 17q23 probes (Barlund et al., *Genes Chrom. Cancer* 20:372–376 (1997)). Before hybridization, tumor array sections were deparaffinized, air dried and dehydrated in 70, 85 and 100% ethanol followed by denaturation for 5 minutes at 74° C. in 70% formamide-2×SSC solution. The hybridization mixture contained 30 ng of each of the probes and 15 µg of human Cot1-DNA. After overnight hybridization at 37° C. in a humidified chamber, slides were washed and counterstained with 0.2 µM DAPI in an antifade solution. FISH signals were scored with a Zeiss fluorescence microscope equipped with double-band pass filters for simultaneous visualization of FITC and Spectrum Orange signals. Over 10 FISH signals per cell or tight clusters of signals were considered as criteria for gene amplification.

EXAMPLE 4 mRNA In Situ Hybridization

For mRNA in situ hybridization, tumor array sections were deparaffinized and air dried before hybridization. Synthetic oligonucleotide probes directed against erbB2 mRNA (Genbank accession number X03363, nucleotides 350–396) was labeled at the 3'-end with $^{33}$P-dATP using terminal deoxynucleotidyl transferase. Sections were hybridized in a humidified chamber at 42° C. for 18 hours with $1\times10^7$ CPM/ml of the probe in 100 µL of hybridization mixture (50% formamide, 10% dextran sulfate, 1% sarkosyl, 0.02 M sodium phosphate, pH 7.0, 4×SSC, 1×Denhardfs solution and 10 mg/ml ssDNA). After hybridization, sections were washed several times in 1×SSC at 55° C. to remove unbound probe, and briefly dehydrated. Sections were exposed for three days to phosphorimager screens to visualize ERBB2 mRNA expression. Negative control sections were treated with RNase prior to hybridization, which abolished all hybridization signals.

The present method enables high throughput analysis of hundreds of specimens per array. This technology therefore provides an order of magnitude increase in the number of specimens that can be analyzed, as compared to prior blocks where a few dozen individual formalin-fixed specimens are in a less defined or undefined configuration, and used for antibody testing. Further advantages of the present invention include negligible destruction of the original tissue blocks, and an optimized fixation protocol which expands the utility of this technique to visualization of DNA and RNA targets. The present method also permits improved procurement and distribution of human tumor tissues for research purposes. Automation of the procedure permits efficient specimen sampling and array formation into multiple tissue arrays, each providing as many as 50, 100 or even up to 200 sections for molecular analysis. Entire archives of tens of thousands of existing formalin-fixed tissues from pathology laboratories can be placed in a few dozen high-density tissue microarrays to survey many kinds of tumor types, as well as different stages of tumor progression. The tumor array strategy also allows testing of dozens or even hundreds of potential prognostic or diagnostic molecular markers from the same set of tumors. Alternatively, the cylindrical tissue samples provide specimens that can be used to isolate DNA and RNA for molecular analysis.

In view of the many possible embodiments to which the principles of our invention may be applied, it should be recognized that the illustrated embodiments are preferred examples of the invention, and should not be taken as a limitation on the scope of the invention. Rather, the scope of the invention is defined by the following claims. We therefore claim as our invention all that comes within the scope and spirit of these claims.

We claim:

1. An apparatus for preparing specimens for parallel analysis of sections of biological material arrays, comprising:
   a donor block holder for holding a tissue donor block in a donor position; and
   a first reciprocating punch positioned in relation to the holder to punch a tissue specimen from the tissue donor block when the donor block is in the donor position;
   a recipient block holder for holding a recipient block in a recipient position, wherein the recipient block comprises an array of receptacles, each of which is positionable in a preselected position in relation to the first reciprocating punch to deliver a tissue specimen from the first reciprocating punch into a receptacle in the preselected position; and
   a second reciprocating punch capable of being positioned relative to the recipient block for punching the array of receptacles in the recipient block, wherein the second reciprocating punch is different than the first reciprocating punch positioned to punch the specimen from the tissue donor block; and
   a positioner for positioning over the donor block a reference slide that includes at least one structure of interest, to align the at least one structure of interest in the reference slide with corresponding tissue specimen regions in the donor block.

2. The apparatus of claim 1, wherein the recipient block bolder comprises an x-y positioning device that can be incrementally moved to align sequential receptacles and the reciprocating punch.

3. The apparatus of claim 1, further comprising a stylet positioned for introduction into the reciprocating punch to expel the tissue specimen from the punch into one of the receptacles aligned with the punch.

4. The apparatus of claim 1, wherein the diameter of the first reciprocating punch positioned to punch the specimen from the tissue donor block is greater than the diameter of the second reciprocating punch.

5. The apparatus of claim 1, further comprising a microscope configured for observing the reference slide.

6. An apparatus for preparing specimens for parallel analysis of sections of biological material arrays, comprising:

a donor block holder for holding a tissue donor block in a donor position; and a first reciprocating punch positioned in relation to the holder to punch a tissue specimen from the tissue donor block when the donor block is in the donor position; and a recipient block holder for holding a recipient block in a recipient position, wherein the recipient block comprises an array of receptacles, each of which is positionable in a preselected position in relation to the first reciprocating punch to deliver a tissue specimen from the first reciprocating punch into a receptacle in the preselected position; and a second reciprocating punch capable of being positioned relative to the recipient block for punching the array of receptacles in the recipient block, wherein the second reciprocating punch is different than the fist reciprocating lunch positioned to punch the specimen from the tissue donor block; and a recorder for recording coordinate positions of the receptacles in the recipient block.

7. The apparatus of claim 6, wherein the recorder is a computer implemented system for recording the positions of the receptacles, and recording an identification of the tissue specimen that is placed in each receptacle.

8. The apparatus of claim 7 wherein the identification includes information about the biological material that is not obtained from analysis of sections of the biological material.

9. The apparatus of claim 6, wherein the diameter of the first reciprocating punch positioned to punch the specimen from the tissue donor block is greater than the diameter of the second reciprocating punch.

10. An apparatus for preparing specimens for parallel analysis of sections of biological material arrays, comprising:

a donor block holder for holding a tissue donor block in a donor position; and a first reciprocating punch positioned in relation to the holder to punch a tissue specimen from the tissue donor block when the donor block is in the donor position; and a recipient block holder for holding a recipient block in a recipient position, wherein the recipient block comprises an array of receptacles, each of which is positionable in a preselected position in relation to the first reciprocating punch to deliver a tissue specimen from the first reciprocating punch into a receptacle in the preselected position; and a second reciprocating punch capable of being positioned relative to the recipient block for punching the array of receptacles in the recipient block, wherein the second reciprocating punch is different than the first reciprocating punch positioned to punch the specimen from the tissue donor block; and a sectioning device for sectioning the recipient block into sections that can be subjected to different analyses.

11. The apparatus of claim 10, further comprising a recorder for recording results of the different analyses in association with information about the biological material that is not obtained from analysis of the sections themselves.

12. The apparatus of claim 10, wherein the diameter of the first reciprocating punch positioned to punch the specimen from the tissue donor block is greater than the diameter of the second reciprocal punch.

13. An apparatus for preparing specimens for parallel analysis of sections of biological material arrays, comprising:

a donor block holder for holding a tissue donor block in a donor position; and a first reciprocating punch positioned in relation to the holder to punch a tissue specimen from the tissue donor block when the donor block is in the donor position; and a recipient block holder for holding a recipient block in a recipient position, wherein the recipient block comprises an array of receptacles, each of which is positionable in a preselected position in relation to the it reciprocating punch to deliver a tissue specimen from the first reciprocating punch into a receptacle in the preselected position; and a second reciprocating punch capable of being positioned relative to the recipient block for punching the array of receptacles in the recipient block, wherein the second reciprocating punch is different than the first reciprocating punch positioned to punch the specimen from the tissue donor block; and a reference slide positioner that includes at least one slide that extends between opposing walls of the donor block holder.

14. A device for preparing biological material arrays, comprising:

a platform that includes at least one guide for positioning a tissue donor block holder or a recipient block holder; and a punch apparatus that includes it guide surface, a punch base slidably mounted on the guide surface, an a punch received within the punch base that can he aligned with the tissue block holder or the recipient block holder; and a reference slide positioner interposed between the platform and the punch apparatus.

15. The device of claim 14, further comprising means for sliding the punch base.

16. An integrated apparatus for preparing specimens for parallel analysis of sections of biological material arrays, comprising:

a donor block holder that can hold a tissue donor block in a donor position;

a first reciprocal punch positioned in relation to the donor block holder that can punch a tissue specimen from the tissue donor block when the donor block is in the donor position;

a recipient block holder that can hold a recipient block in a recipient position, wherein the recipient block comprises an array or receptacles, each of which is positionable in a preselected position in relation to the first reciprocal punch to deliver a tissue specimen from the first reciprocal punch into a receptacle in the preselected position; and a second reciprocal punch capable of being positioned relative to the recipient block for punching the array of receptacles in the recipient block, wherein the second reciprocal punch is different than the first reciprocal punch positioned to punch the specimen from the tissue donor block; and a positioner that can position over the donor block a reference slide that includes at least one structure of interest to align the at least one structure of interest in the reference slide with corresponding tissue specimen regions in the donor block.

17. The apparatus of claim 16, further comprising z-direction positioning means for the first reciprocal punch and the second reciprocal punch.

18. The apparatus of claim 16, wherein the diameter of the first reciprocating punch positioned to punch the specimen from the tissue donor block is greater than the diameter of the second reciprocating punch.

19. An apparatus for preparing specimens for parallel analysis of sections of biological material arrays, comprising:

an x-y positioning platform;

a donor block holder for holding a tissue donor block in a donor position, the donor block holder being disposed on the x-y positioning platform;

a reciprocating punch positioned in relation to the donor block holder to punch a tissue specimen from the tissue donor block when the donor block is in the donor position;

a recipient block holder for holding a recipient block in a recipient position, wherein the recipient block comprises an array of receptacles, each of which is positionable in a preselected position in relation to the reciprocating punch to deliver a tissue specimen from the reciprocating punch into a receptacle in the preselected position, the recipient block holder being disposed on the x-y positioning platform;

a sectioning device for sectioning the recipient block into sections that can be subjected to different analyses; and z-direction positioning means for the reciprocating punch.

20. An apparatus for preparing specimens for parallel analysis of sections of biological material arrays, comprising:

an x-y positioning platform;

a donor block holder for holding a tissue donor block in a donor position, the donor block holder being disposed on the x-y positioning platform;

a reciprocating punch positioned in relation to the donor block holder to punch a tissue specimen from the tissue donor block when the donor block is in the donor position;

a recipient block holder for holding a recipient block in a recipient position, wherein the recipient block comprises an array of receptacles, each of which is positionable in a preselected position in relation to the reciprocating punch to deliver a tissue specimen from the reciprocating punch into a receptacle in the preselected position, the recipient block holder being disposed on the x-y positioning platform;

a recorder for recording coordinate positions of the receptacles in the recipient block; and z-direction positioning means for the reciprocating punch.

* * * * *

UNITED STATES PATENT AND TRADEMARK OFFICE
CERTIFICATE OF CORRECTION

PATENT NO. : 6,699,710 B1
DATED : March 2, 2004
INVENTOR(S) : Juha Kononen, Stephen B. Leighton and Olli P. Kallioniemi It is certified that error appears in the above-identified patent and that said Letters Patent is hereby corrected as shown below:

Title page,
Item [75], Inventors, change "Olli-P. Kallioniemi" to -- Olli P. Kallioniemi --.

Signed and Sealed this

Seventh Day of February, 2006

JON W. DUDAS
*Director of the United States Patent and Trademark Office*